United States Patent [19]

Gauthier-Lafaye et al.

[11] 4,306,091

[45] Dec. 15, 1981

[54] PROCESS FOR THE PREPARATION OF ACETALDEHYDE

[75] Inventors: Jean Gauthier-Lafaye, Lyons; Robert Perron, Charly, both of France

[73] Assignee: Rhone-Poulenc Industries, Paris, France

[21] Appl. No.: 164,332

[22] Filed: Jun. 30, 1980

[30] Foreign Application Priority Data

Jul. 4, 1979 [FR] France ............................ 79 17927

[51] Int. Cl.³ ...................... C07C 47/06; C07C 45/49
[52] U.S. Cl. ..................................... 568/487; 568/489
[58] Field of Search ..................... 568/487, 489, 496

[56] References Cited

U.S. PATENT DOCUMENTS

| | | | |
|---|---|---|---|
| 2,727,902 | 12/1955 | Reppe et al. | 568/487 |
| 2,729,651 | 1/1956 | Reppe et al. | 568/487 |
| 3,248,432 | 4/1966 | Riley | 568/487 |
| 3,285,948 | 11/1966 | Butter | 568/487 |
| 3,356,734 | 12/1967 | Kuraishi | 568/487 |
| 4,126,752 | 11/1978 | Novotny et al. | 568/902 |
| 4,133,966 | 1/1979 | Pretzer et al. | 568/902 |
| 4,151,208 | 4/1979 | Pretzer et al. | 568/487 |
| 4,171,461 | 10/1979 | Bartish | 568/902 |
| 4,190,729 | 2/1980 | Forster | 568/487 |
| 4,225,517 | 9/1980 | Gane | 568/487 |
| 4,233,466 | 11/1980 | Fiato | 568/902 |

FOREIGN PATENT DOCUMENTS

| | | | |
|---|---|---|---|
| 48-2525 | 1/1973 | Japan | 568/487 |
| 52-133914 | 11/1977 | Japan . | |
| 52-136111 | 11/1977 | Japan . | |
| 1546428 | 5/1979 | United Kingdom . | |

OTHER PUBLICATIONS

Wender et al., "Science", vol. 113, p. 206, (1951).
Berry et al., "Chem. Tech.", vol. 5, pp. 260–266, (1966).
Mizoroki et al., "Bull. Chem. Soc. Jap.", vol. 52(2), pp. 479–482, (1979).

Primary Examiner—Werren B. Lone

[57] ABSTRACT

A process for the carbonylation of methanol to produce acetaldehyde comprising reacting methanol in the presence of hydrogen, cobalt, ruthenium, at least one ionic halide, and at least one alkyl halide, the molar ratio Ru/Co being at most equal to about 2, and the cobalt concentration being at most about 50 milligram atoms per liter of reaction medium.

20 Claims, No Drawings

PROCESS FOR THE PREPARATION OF ACETALDEHYDE

BACKGROUND OF THE INVENTION

The present invention relates to an improved process for the preparation of acetaldehyde by carbonylation of methanol in the presence of hydrogen.

Acetaldehyde is an intermediate of great interest in the chemical industry. It is, in particular, useful for the manufacture of acetic acid and of acetic anhydride (cf. "Encyclopedia of Chemical Technology," Kirk-Othmer, 3rd edition, Vol. 1, pages 97 et seq.).

Industrial processes for producing acetaldehyde have been developed. The process most used at the present time is direct oxidation of ethylene. However, since this hydrocarbon originates from petroleum, it may become more economical to choose starting materials originating from synthesis gas, such as methanol.

The use of methanol as a starting material in the synthesis of products which traditionally are produced on an industrial scale from ethylene has formed the subject, and continues to be the subject, of numerous research projects. These research projects essentially concern the application of carbonylation techniques, that is to say, the reaction of carbon monoxide with methanol, where appropriate, in the presence of hydrogen.

Thus, numerous earlier investigations have concerned the homologisation of methanol, ie., the production of ethanol by carbonylation of methanol.

It is well known that methanol reacts with a 1 to 1 mixture of carbon monoxide and hydrogen at 185° C., and under 360 atmospheres pressure, in the presence of dicobalt octacarbonyl. Under these conditions, a mixture of various products, containing ethanol, is obtained, the selectivity in respect of ethanol being relatively low (cf. Wender et al, "Science," Vol. 113, page 206, 1951).

Other authors have shown that when the homologisation reaction is carried out at 200° C. under 200–350 atmospheres pressure in the presence of cobalt diacetate, the yield of ethanol can be improved by the simultaneous measures of operating in the presence of an iodine-containing promoter ($I_2$ or $CH_3I$) and using a gas mixture rich in carbon monoxide (cf. Berty et al., "Chem. Tech.," Vol. 5, pages 260–266, 1956).

Further progress towards the production of ethanol has been achievable by addition of a methanol-soluble, phosphorus-containing compound to the preceding catalyst system (cf. French Pat. No. 1,341,840), by introducing ruthenium halides or osmium halides (cf. U.S. Pat. No. 3,285,948) or by addition of a tertiary phosphine and a hydrocarbon as a solvent (cf. French Pat. No. 2,314,166).

However, these processes are not applicable on an industrial scale. They do not make it possible to achieve high selectivities in respect of ethanol and, consequently, necessitate the setting up of complex installations for separating the various constituents of the mixture obtained, which unacceptably worsens the overall economics of such a process.

Starting from this observation, other investigators have concerned themselves with the production of acetaldehyde. Thus, it has been stated that the presence of an amount of cobalt of less than 2 millimols per mol of methanol in the catalyst system (cobalt/halogen) favors the conversion of methanol to acetaldehyde (cf. U.S. Pat. No. 3,356,734).

In effect, if the carbonylation of methanol is carried out in accordance with the technique which forms the subject of the above-mentioned U.S. patent, at 185° C. under 300–400 atmospheres pressure, with a $CO/H_2$ molar ratio of 1.4, for 2 hours, about 130 g. of acetaldehyde per liter of reaction medium per hour are obtained, the productivity being of the order of 70 g. of acetaldehyde per hour per gram of cobalt involved in the reaction, allowing for the fact that the dimethoxyethane formed is a potential source of acetaldehyde More recent work (cf. Japanese patent applications Nos. 77/136,111 and 77/133,914) has shown that the results achieved with this catalyst system can be substantially improved by adding to the system (cobalt/iodine) a substantial quantity of a phosphorus-containing compound or of a compound of arsenic, antimony, or bismuth. Nevertheless, the productivity in respect of acetaldehyde, relative to the cobalt employed, remains low, in site of the high pressures employed. Furthermore, in the known processes, a not insignificant part of the methanol is converted to butanol, butanal, and butenal, which are products for which demand is irregular, and which worsen the overall economics of the process by necessitating supplementary separation steps. Furthermore, the possibility of industrial exploitation of such processes is hampered by the high pressure required to achieve acceptable hourly productivities. Certain authors (cf. T. Mizoroki et al., "Bull. Chem. Soc. Jap.," Vol. 52(2), 479, 1979) have studied the carbonylation of methanol in the presence of cobalt and of methyl iodide, in methyl benzoate and under about 150 bars pressure. They have confirmed that under these conditions, the addition of small amounts of ruthenium substantially increases the selectivity in respect of ethanol, at the expense of acetaldehyde. They have also shown the overwhelming role played by sodium iodide in this reaction. Nevertheless, the hourly productivity of acetaldehyde does not exceed 65 g. per hour per liter of reaction medium and only reaches 14 g. per hour per gram of cobalt employed in the reaction.

It has now been found, totally unexpectedly, that the addition of small amounts of ruthenium to a catalyst system having a low cobalt content makes it possible considerably to increase the performance characteristics of the said system, thus permitting the selective production of acetaldehyde by hydrocarbonylation of methanol, with a remarkable hourly productivity, under a total pressure as low as 100 bars.

It is, therefore, an object of the present invention to provide a novel process for the homologisation of methanol to produce acetaldehyde in commercially practical yields.

It is also an object of the present invention to provide a process for producing acetaldehyde from methanol by homologisation which employs practical pressures.

Other objects will be apparent to those killed in the art from the present description.

GENERAL DESCRIPTION OF THE INVENTION

The present invention relates to a process for the hydrocarbonylation of methanol in the simultaneous presence of at least one ionic halide, at least one alkyl halide, at most about 50 milligram atoms of cobalt per liter of reaction mixture, and at most about 2 gram atoms of ruthenium per gram atom of cobalt present in the mixture, the temperature being at least bout 180° C.

The process according to the invention requires the use of at least one ionic halide. The term "ionic halide" is understood to mean those inorganic or organic clorides, bromides, or, preferably, iodides. The cations of these halides are preferably chosen from among alkali metal cations, alkaline earth metal cations, and the quaternary ammonium or phosphonium cations represented by the formulae I to III, below:

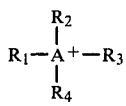   (I)

in which A represents a nitrogen or phosphorus atom and $R_1$, $R_2$, $R_3$, and $R_4$, which may be identical or different, represent hydrogen, or preferably, organic radicals in which the free valency is carried by a carbon atom; optionally, any two of these radicals may together form a single divalent radical.

More specifically, $R_1$, $R_2$, $R_3$, and $R_4$, may represent linear or branched alkyl radicals or monocyclic cycloalkyl, aralkyl (for example, benzyl), or aryl radicals, which have, at most, about 16 carbon atoms and which may be substituted by about 1 to 3 alkyl radicals having from about 1 to 4 carbon atoms; optionally, two of the radicals $R_1$ to $R_4$ may together form a single, divalent, alkylene, or alkenylene radical containing about 3 to 6 carbon atoms (for example, a tetramethylene or hexamethylene radical) and, optionally, about b 1 or 2 ethylenic double bonds, it being possible for the said radical to carry about 1 to 3 alkyl substituents having from about 1 to 4 carbon atoms:

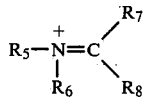   (II)

in which $R_5$, $R_6$, $R_7$, and $R_8$, which are identical or different, represent alkyl radicals having from about 1 to 4 carbon atoms, it further being possible for one of the radicals $R_7$ or $R_8$ to represent hydrogen, and it being possible, optionally, for $R_7$ and $R_8$ together to form a single, divalent alkylene radical containing from about 3 to 6 carbon atoms, for example, a tetramethylene or hexamethylene radical; $R_6$ and $R_7$ or $R_8$ may together form a single, divalent, alkylene or alkenylene radical containing 4 carbon atoms and, optionally, about 1 or 2 ethylenic double bonds, the nitrogen atom then being included in a heterocyclic ring in order to form, for example, a pyridinium cation:

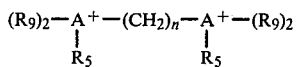   (III)

in which $R_5$ and $A^+$ have the meaning given above, $R_9$, which may be identical to $R_5$, represents an alkyl radical having from about 1 to 4 carbon atoms, or a phenyl radical, and n is an integer between about 1 and 10 ($1 \leq n \leq 10$) and preferably between about 1 and 6 ($1 \leq n \leq 6$).

Examples which may be mentioned of quaternary ammonium halides which are suitable for carrying out the present process are tetramethylammmonium, triethylmethylammonium, tributylmethylammonium, trimethy-(n-propyl)ammonium, tetraethylammonium, tetrabutylammonium, dodecyltrimethylammonium, benzyltrimethylammonium, benzyldimethylproxylammonium, benzyldimethyloctylammonium, dimethydiphenylammonium, methyltriphenylammonium, N,N-dimethyltrimethyleneammonium, N,N-diethyl-trimethyleneammonium, N,N-dimethyltetramethyleneammonium, N,N-diethyl-tetramethyleneammonium, N-methylpyridinium, N-ethylpyridinium, and N-methylpicolinium chlorides, bromides, and, more particularly, iodides.

Examples which may be mentioned of quaternary phosphonium halides which are also suitable for carrying out the present process are tetramethylphosphonium, ethyltrimethylphosphonium, trimethylpentylphosphonium, octyltrimethylphosphonium, dodecyltrimethylphosphonium, trimethylphenylphosphonium, diethyldimethylphosphonium, dicyclohexyldimethylphosphonium, dimethyldiphenylphosphonium, cyclohexyltrimethylphosphonium, triethylmethylphosphonium, methyl-tri-(isopropyl)-phosphonium, methyl-tri-(n-propyl)-phosphonium, methyl-tri-(n-butyl)-phosphonium, methyl-tris (2-methylpropyl)-phosphonium, methyltricyclohexylphosphonium, methytriphenylphosphonium, methyltribenzylphosphonium, methyl-tris-(4-methylphenyl)-phosphonium, methyltrixylylphosphonium, diethylmethylphenylphosphonium, dibenzylmethylphenylphosphonium, ethyltriphenylphosphonium, tetraethylphosphonium, ethyl-tri-(n-propyl)-phosphonium, triethylpentylphosphonium, ethyltriphenylphosphonium, n-butyl-tri-(n-propyl)-phosphonium, butyltriphenylphosphonium, benzyltriphenylphosphonium, ($\beta$-phenylethyl)-dimethylphenylphosphonium, tetraphenylphosphonium, and triphenyl-(4-methylphenyl)-phosphonium chlorides, bromides, and more particularly, iodides.

The specific quaternary ammonium or phosphonium cation employed is not of fundamental importance within the scope of the process of the present invention. The choice from among these compounds is governed more by practical considerations, such as the solubility in the reaction medium, the availability and the convenience of use. In this respect, the quaternary ammonium or phosphonium halides represented either by the formula (I) in which any one of the radicals $R_1$ to $R_4$ is chosen from among linear alkyl radicals having from about 1 to 4 carbon atoms, or by the formulae (II) or (III) in which $R_5$ (or $R_6$) is also an alkyl radical having from about 1 to 4 carbon atoms, are particularly suitable.

Moreover, the preferred ammonium halides are those in which the cations correspond to the formula (I) in which all the radicals $R_1$ to $R_4$ are chosen from among linear alkyl radicals which have from about 1 to 4 carbon atoms and at least three of which are identical.

Likewise, the preferred quaternary phosphonium halides are those in which the cations correspond to the formula (I) in which any one of the radicals $R_1$ to $R_4$ represents a linear alkyl radical having from about 1 to 4 carbon atoms, the other three radicals being identical and being chosen from among phenyl, tolyl, or xylyl radicals.

The quaternary phosphonium iodides, and more particularly, those in which the cations correspond to the formula (I), above, in which one of the radicals $R_1$ to $R_4$ is an alkyl radical having from about 1 to 4 carbon atoms, the other three radicals being identical and being chosen from among phenyl, tolyl, or xylyl radicals, constitute a class of ionic halides which are particularly convenient for practicing the present invention.

A preferred embodiment of the present invention comprises the use of alkali-metal or alkaline earth metal iodides, such as: LiI, NaI, KI, CsI, $CaI_2$ and $MgI_2$. Preferably, one or more alkali-metal iodides are used; even more advantageously, NaI or KI is used.

According to the present invention, the molar ratio $X^-/Co$, $X^-$ being the halide ion originating from the ionic halide, should be equal to at least about 5. It is not desirable for this ratio to exceed a value of about 400. Very satisfactory results are obtained for a ratio $X^-/CO$ of the order of about 5 to 150.

The process of the invention also requires the use of at least one alkyl halide, that is to say, a compound of the formula RX, in which X represents a chlorine or bromine atom or, preferably, an iodine atom, and R is an alkyl radical having a maximum of about 16 carbon atoms. Of course, the methyl halides which can initially be introduced into the reaction medium are capable of being formed in situ from halogen derivatives, such as $Cl_2$, $Br_2$, $I_2$, HCl, HBr, HI, $CoBr_2$, $CoI_2$, $RuCl_3$, and $RuI_3$, with methanol (starting material). In other words, all or part of the methyl halide necessary for carrying out the present process can be formed from the precursors defined above.

It will also be seen that, if the halogen derivative is chosen from among the cobalt compounds or the ruthenium compounds, it can be considered not only as a precursor of the methyl halide, but also a precursor of the metal catalyst (or catalysts). In this particular case, it proves preferable also to introduce, initially, an alkyl halide and/or a precursor of the methyl halide, which is different from the metal halides in question.

The invention envisages, in particular, the use of lower alkyl chlorides, bromides and iodides having from about 1 to 4 carbon atoms in the molecule, such as methyl bromide and iodide, ethyl bromide and iodide, and propyl bromide and iodide. Methyl iodide and/or one of its potential sources chosen from among iodine, hydriodic acid, cobalt iodide, and ruthenium iodide, is preferably used.

An additional advantage of the present invention resides in the possibility of operating with contents of the halogen X, originating from the alkyl halide, which are as low as about 5 millimols per liter of reaction medium. It is desirable not to exceed a value of about 200 millimols for this content, especially in order to restrict corrosion of the equipment. Good results are obtained with a content in the order of 10 to 100 millimoles of X per liter.

The process of the invention is carried out in the presence of cobalt. Any source of cobalt capable of reacting with carbon monoxide in the reaction medium to give cobalt complexes can be used within the scope of the present invention. Typical suitable sources of cobalt are, for example, finely divided cobalt metal, inorganic salts, such as cobalt carbonate, and organic salts, in particular, fatty acid salts. Cobalt carbonyls, cobalt hydrocarbonyls or their complexes can also be employed. Among the cobalt derivatives suitable for carrying out the process according to the invention, cobalt acetate and formate, cobalt halides, in particular, cobalt iodide, and dicobalt octacarbonyl may be mentioned.

A characteristic of the present process is that amounts of cobalt of less than about 50 milligram atoms per liter of reaction medium are employed. This content can be as low as 0.1 milligram atom per liter, and is preferably between about 0.5 and 30 milligram atoms per liter.

The process according to the invention also requires the presence of ruthenium. The precise form in which the ruthenium is employed in the reaction is not of fundamental importance within the scope of the present invention. Ruthenium metal in a finely divided form, or ruthenium compounds, such as $RuCl_3$, $RuI_3$, $RuO_2$, $Ru_3(CO)_{12}$ and $Ru(C_5H_7O_2)_3$, can be used.

The amount of ruthenium to be employed within the scope of the present process is at most about 2 gram atoms of ruthenium per gram atoms of cobalt employed in the reaction. Preferably, the ratio of ruthenium to cobalt is between about 0.01 and 1.

The carbonylation process of the present invention is preferably, but not necessarily, carried out in the liquid phase. As the reaction is most frequently carried out with the methanol in excess, the simultaneous use of an additional solvent is generally superfluous, but, in principle, it is possible to use such solvents, for example, hydrocarbons, esters, ether, and the reaction products.

Within the scope of the present process, it is not necessary to purify or dry the methanol beforehand. Technical grade methanol, containing, for example, water, can be used.

In accordance with the present process, a mixture of carbon monoxide and hydrogen is reacted with the methanol. It is essential for the said mixture to contain at least about 25 mol percent of hydrogen. In general, mixtures containing up to about 95 mol percent of hydrogen can be used. Mixtures containing from about 40 to 80 mol percent of hydrogen are preferably used. The mixture of gases can contain impurities, such as, for example, carbon dioxide, oxygen, methane and nitrogen.

The reaction is carried out under a total pressure which is generally between about 50 and 600 bars. Preferably, this pressure is between about 75 and 300 bars and more particularly, between about 100 and 250 bars.

The reaction temperature is at least about 180° C. and can reach about 240° C., if the reaction is carried out without a solvent. In the case where a solvent is used, and this remains optional within the scope of the present invention, the temperature can reach about 300° C. Preferably, the reaction is carried out in a temperature range of about 180° to 230° C.

SPECIFIC DESCRIPTION OF THE INVENTION

In order to disclose more clearly the nature of the present invention, the following examples illustrating the invention are given. It should be understood, however, that this is done solely by way of example and is intended neither to delineate the scope of the invention nor limit the ambit of the appended claims. In the examples which follow, and throughout the specification, the quantities of material are expressed in terms of parts by weight, unless otherwise specified.

EXAMPLES

Working Method

The methanol, a solvent where appropriate, and the components of the catalyst system were charged into an autoclave made of Z8-CNDT 17–12 (AFNOR Stanard Specification) stainless steel, and having a capacity of 250 ml. (The sources of cobalt and ruthenium were, unless stated otherwise, respectively, dicobalt octacarbonyl and triruthenium dodecacarbonyl.)

After closing the autoclave, an initial pressure, the value of which will be stated below, was established by means of a $CO/H_2$ mixture, of which the composition will also be stated for each experiment. Agitation, by means of a reciprocating system, was started and the autoclave was raised to the desired temperature in about 25 minutes, by means of an annular furnace. The pressure in the autoclave was maintained by periodically recharging it with a mixture of $CO/H_2$, the composition of which, unless stated otherwise, was identical to that of the mixture which was used to establish the initial pressure. After a certain period of reaction at the temperature indicated, heating and agitation were stopped and the autoclave was cooled and let down.

The resulting reaction mixture was diluted and analyzed by gas chromotography.

The data in g./hr.×l. (liter) and g./hr.×g. (gram) (Co) express the productivity in grams of acetaldehyde per hour of reaction time, respectively, per liter of reaction volume and per gram of cobalt employed in the reaction.

EXAMPLE 1

The following were introduced into an autoclave as described above, and using the working method described above: 95 ml. of methanol, 5 ml. of water, 509 mg. (3.58 millimols) of methyl iodide, 1.8 g. (12 millimoles) of sodium iodide, 0.126 milligram atom of cobalt, in the form of 21.6 mg. of dicobalt octacarbonyl, and 0.117 milligram atom of ruthenium, in the form of 25 mg. of triruthenium dodecacarbonyl.

An initial pressure of 140 bars was established by means of an equimolecular mixture of CO and $H_2$. The autoclave was raised to a temperature of 215° C. The pressure in the autoclave was maintained at between 230 and 260 bars by periodically recharging the autoclave with a 1:2 (molecular) $CO/H_2$ mixture.

After 1 hour, 15 minutes of reaction time, 24.7 g. of acetaldehyde were obtained, representing a productivity of 200 g./hr.×l. (liter) and of 2,600 g./hr.×g. (Co).

The two comparative experiments below do not fall within the scope of the present invention and are only given by way of comparison.

Comparative Experiment "A"

Example 1, above, was repeated, omitting the triruthenium dodecacarbonyl. 14.1 g. of acetaldehyde were obtained, corresponding to a productivity of the order of 110 g./hr.×l. and of 1,400 g./hr.×g. (Co). It is found that in the absence of ruthenium, the hourly productivity dropped considerably.

Comparative Experiment "B"

Using the working method described above, 95 ml. of methanol, 1.5 ml. of water, 3.58 millimols of methyl iodide, 12 millimoles of sodium iodide, and 0.66 milligram atom of ruthenium, in the form of triruthenium dodecacarbonyl, were charged into the autoclave.

After 1 hour, 30 minutes of reaction time at 210° C., the pressure in the autoclave being kept at between 230 and 260 bars by periodically recharging with an equimolecular mixture of CO and $H_2$, only 0.7 g. of acetaldehyde was obtained.

It is found that the ruthenium had virtually no catalytic effect in the process proposed. If Example 1 and Comparative Experiment "A" are compared, the remarkable effect produced by very small amounts of ruthenium added to the catalyst system based on cobalt is observed, this effect being obsolutely unexpected if the negative results obtained in Comparative Experiment "B" are considered.

EXAMPLE 2

An initial pressure of 140 bars was established, by means of a 2:3 (molecular) $CO/H_2$ mixture, over a charge consisting of 0.123 milligram atom of cobalt, 0.113 milligram atom of ruthenium, 12 millimols of tetrabutylammonium bromide, 1.5 millimols of methyl iodide, and 100 ml. of methanol. 5.2 g. of acetaldehyde were obtained after 40 minutes of reaction time at a temperature of 205° C., the pressure in the autoclave being kept at between 245 and 260 bars. It was found that 78 percent of the methanol converted is transformed to acetaldehyde; the main by-products are the following: ethanol (0.4 g.), methyl ethyl ether (0.4 g.), and methyl acetate (0.6 g.).

EXAMPLE 3

An initial pressure of 140 bars was set up by means of a 2:3 (molecular) $CO/H_2$ mixture, over a charge consisting of 100 ml. of methanol, 2.4 millimols of ethyl bromide, 0.108 milligram atom of ruthenium, 11 millimols of lithium iodide, and 0.120 milligram atom of cobalt. 10.1 g. of acetaldehyde were obtained after 40 minutes of reaction time at a temperature of 185° C., the pressure in the autoclave being kept at between 185 and 245 bars. It was found that 84 mol percent of the methanol converted was to acetaldehyde.

EXAMPLE 4

An initial pressure of 140 bars was established by means of a 2:3 (molecular) $CO/H_2$ mixture over a charge consisting of 0.130 milligram atom of cobalt, 0.125 milligram atom of ruthenium, 12 millimols of triphenylmethylphoshonium iodide, 1.6 millimols of methyl iodide, and 100 ml. of methanol. After 40 minutes of reaction time at a temperature of 205° C., the pressure in the autoclave being kept at between 230 and 260 bars, 19.5 g. of acetaldehyde were obtained, representing a productivity of 290 g./hr.×l. and of 3,800 g./hr.×g. (Co).

It was found that 84 mol percent of the methanol converted was converted to acetaldehyde. The amount of ethanol present was found to be less than 1 g.

EXAMPLE 5

An initial pressure of 140 bars was established by means of an equimolecular $CO/H_2$ mixture over a charge consisting of 100 ml. of methanol, 1.17 millimols of ethyl iodide, 12 millimols of sodium iodide, 0.116 milligram atom of ruthenium, and 0.128 milligram atoms of cobalt. After 40 minutes of reaction time at a temperature of 205° C., the pressure in the autoclave being kept at between 230 and 260 bars, 20.7 g. of acetaldehyde were obtained, representing a productivity of 310 g./hr.×l. and 4,100 g./hr.×g. (Co).

It was found that 81 mol percent of the methanol converted was converted to acetaldehyde.

EXAMPLE 6

An initial pressure of 140 bars was established by means of an equimolecular $CO/H_2$ mixture over a charge consisting of 0.126 milligram atom of cobalt, 0.121 milligram atom of ruthenium, 12 millimols of sodium iodide, 1.72 millimols of methyl iodide, and 100 ml. of methanol. After 1 hour, 15 minutes of reaction time at a temperature of 215° C., the pressure in the autoclave being kept at between 230 and 260 bars, 27.7 g. of acetaldehyde were obtained.

It was found that 73 mol percent of the methanol converted was converted to acetaldehyde.

EXAMPLES 7 to 11 and Comparative Experiment "C"

An initial pressure of 70 bars, in the case of Examples 10 and 11, and of 40 bars, in the case of the other examples, as well as in Comparative Experiment "C" (below), was established by means of a 2:3 (molecular) $CO/H_2$ mixture, over a charge containing 100 ml. of methanol, 12 millimols of tributylmethylphosphonium iodide, and various amounts of methyl iodide, dicobalt octacarbonyl, and triruthenium dodecacarbonyl. The reaction time at 205° C. was 40 minutes, the pressure in the autoclave being kept at between 140 and 155 bars in the case of Examples 10 and 11, and between 95 and 105 bars in the case of the other examples, as well as in the case of Comparative Experiment "C." The specific conditions, as well as the results obtained, are shown in the table below.

It was found in all cases that from 80 to 90 mol percent of the methanol converted was converted into acetaldehyde.

It was found that the particular catalyst system gives remarkable results, in spite of the low pressures employed.

TABLE

| Example No. | Cobalt (milligram atom) | Ruthenium (milligram atom) | $CH_3$ (millimol) | Acetaldehyde (g) | g/hr × l | g/hr × g (Co) |
|---|---|---|---|---|---|---|
| C | 0.56 | 0 | 1.57 | 2.0 | 30 | 90 |
| 7 | 0.55 | 0.057 | 1.44 | 6.0 | 90 | 280 |
| 8 | 0.56 | 0.237 | 1.59 | 6.3 | 96 | 300 |
| 9 | 1.09 | 0.114 | 1.75 | 7.5 | 110 | 180 |
| 10 | 1.13 | 0.115 | 1.75 | 10.9 | 160 | 250 |
| 11 (*) | 1.10 | 0.112 | 3 | 11.5 | 175 | 270 |

(*) Example carried out with sodium iodide (in place of methyltributylphosphonium iodide).

The terms and expressions which have been employed are used as terms of description and not of limitation, and there is no intention in the use of such terms and expressions of excluding any equivalents of the features shown and described or portions thereof, but it is recognized that various modifications are possibe within the scope of the invention claimed.

What is claimed is:

1. A process of producing acetaldehyde by hydrocarbonylating methanol which comprises: reacting methanol with a mixture of carbon monoxide and hydrogen, at a temperature of between about 180° C. and about 300° C. under a total pressure of between about 50 and about 600 bars, in the presence of cobalt and ruthenium, of at least one ionic halide, the cation of which is chosen from the group consisting of alkali-metal cations, alkaline earth metal cations, quaternary ammonium cations, and quaternary phosphonium cations, and of at least one alkyl halide, the alkyl halide having an alkyl radical of up to about sixteen carbon atoms, the molar ratio $X^-/Co$, $X^-$ being the halide ion originating from the ionic halide, being at least about 5, the content of halogen X, X being the halogen originating from the alkyl halide, being at least about 2 millimols per liter of reaction medium, the concentration of cobalt being at most about 50 milligram atoms per liter of reaction medium and the molar ratio of ruthenium to cobalt being at most about 2.

2. A process according to claim 1, wherein the alkyl halide is selected from the among the class consisting of chlorides, bromides, and iodides, having from about 1 to 4 carbon atoms in the molecule.

3. A process according to claim 2, wherein the alkyl halide is a methyl halide.

4. A process according to claim 3, wherein the methyl halide is at least partially produced in situ from at least one compound chosen from the group consisting of molecular chlorine, molecular bromine, and molecular iodine, the corresponding hydrohalic acids, cobalt bromide, and iodide and ruthenium bromide and iodide.

5. A process according to claim 1, wherein the cation of the ionic halide is chosen from among alkali metal cations and alkaline earth metal cations.

6. A process according to claim 1, wherein the ionic halide is an iodide.

7. A process according to claim 1, wherein the alkyl halide is an iodide.

8. A process according to claim 1, wherein the ratio $X^{31}/Co$ is between about 5 and 150.

9. A process according to claim 1, wherein the content of halogen X is between about 10 and 100 millimols per liter of reaction medium.

10. A process according to claim 1, wherein the concentration of the cobalt is between about 0.5 and 30 milligram atoms per liter of reaction medium.

11. A process according to claim 1, wherein the gram atom ratio Ru/Co is between about 0.01 and 1.

12. A process according to claim 1, wherein the total pressure is between about 75 and 300 bars.

13. A process according to claim 1, wherein the temperature is between about 180° and 230° C.

14. A process according to claim 1, wherein said process is conducted in the liquid phase.

15. A process according to claim 1, wherein the mixture of carbon monoxide and hydrogen contains at least about 25 mol percent of hydrogen.

16. A process according to claim 1, wherein the mixture of carbon monoxide and hydrogen contains between about 25 and 95 mol percent of hydrogen.

17. A process according to claim 1, wherein the mixture of carbon monoxide and hydrogen contains from about 40 to 80 mol percent hydrogen.

18. A process according to claim 1, wherein the total pressure is between about 100 and 200 bars.

19. A process according to claim 1 in which a major portion of the methanol converted is converted to acetaldehyde.

20. A process according to claim 1 in which at least about 180 grams of acetaldehyde is produced per hour of reaction time per liter of reaction volume.

* * * * *

UNITED STATES PATENT AND TRADEMARK OFFICE
CERTIFICATE OF CORRECTION

PATENT NO. : 4,306,091
DATED : December 15, 1981
INVENTOR(S) : Gauthier-Lafaye et al.

It is certified that error appears in the above—identified patent and that said Letters Patent is hereby corrected as shown below:

Col. 2, line 21 - "site" should be -- spite --;

Col. 2, line 58 - "killed" should be -- skilled --;

Col. 2, line 68 - "bout" should be -- about --;

Col. 3, line 30 - Delete "b" after "about";

Col. 6, line 66 - "Stanard" should be -- Standard --;

Col. 8, line 3 - "obsolutely" should be -- absolutely --;

Col. 8, line 39 - "triphenylmethylphoshonium" should be
                  -- triphenylmethylphosphonium --;

Col. 9, Table - Over columns 6 & 7 insert the heading
                -- Productivity in --;

Signed and Sealed this

Eighth Day of June 1982

|SEAL|

Attest:

Attesting Officer

GERALD J. MOSSINGHOFF
Commissioner of Patents and Trademarks